United States Patent [19]

Sato

[11] Patent Number: 4,467,199

[45] Date of Patent: Aug. 21, 1984

[54] MACROANALYZER SYSTEM

[75] Inventor: Mitsuyoshi Sato, Tokyo, Japan

[73] Assignee: Seiko Instruments & Electronics Ltd., Tokyo, Japan

[21] Appl. No.: 269,883

[22] Filed: Jun. 3, 1981

[51] Int. Cl.³ .............................................. G01N 23/22
[52] U.S. Cl. ...................................... 250/310; 378/49; 378/83
[58] Field of Search ...................... 378/49, 47, 46, 48, 378/83; 250/310

[56] References Cited

U.S. PATENT DOCUMENTS 3,160,747 12/1964 Vries ........................................ 378/49
3,204,095 8/1965 Watanabe ............................. 250/310
4,037,099 7/1977 Oda ........................................ 378/46

Primary Examiner—Craig E. Church
Attorney, Agent, or Firm—Robert E. Burns; Emmanuel J. Lobato; Bruce L. Adams

[57] ABSTRACT

Macroanalyzer system comprising in combination: a crystal for separating X-ray emitted from a sample, an X-ray detector for detecting X-ray which are separated by the crystal, and a solar slit member located between the crystal, sample and X-ray detector. An operation circuit receives the output of said X-ray detector to eliminate the effect of the X-ray passing through the solar slit.

3 Claims, 9 Drawing Figures

MACROANALYZER SYSTEM

BACKGROUND OF THE INVENTION

This invention relates to a macroanalyzer, particularly, a macroanalyzer which is able to cancel errors caused by a solar slit member through which an X-ray signal passes.

As a conventional analyzer for analyzing an element in a small portion of a metal member, such as slab plate, the X-ray microanalyzer is very well known. However, such a microanalyzer is able to easily analyze a very small portion of a sample but it is not able to analyze a whole or substantial portion of a sample. Since said X-ray microanalyzer uses a curved crystal as an X-ray concentration means, an irradiation point of an electronic beam (X-ray generation point), a spectrocrystal and X-ray detector are necessarily located on a Rowland circle. Therefore in case of an unavoidable irregular portion located on a surface of the sample, for example, a big sample, the X-ray generation point is slipped from the Rowland circle whereby it is very difficult to carry out X-ray detection. Further in case of multi-elements analysis, a part of the Rowland circle is located below a surface of the sample consequently it is not possible to carry out an analysis of the big sample.

SUMMARY OF THE INVENTION

This invention aims to eliminate the above noted difficulty and insufficiency and to provide a macroanalyzer system comprising in combination: a spectrocrystal or diffraction crystal for separating X-ray which be irradiated from a sample or target object to be analyzed, an X-ray detector for detecting X-rays separated by said spectrocrystal, a solar slit member located between said spectrocrystal, sample and X-ray detection and an operation circuit which receives the output of said X-ray detection to eliminate the effect of the X-ray passing through the solar slit member.

DETAILED DESCRIPTION OF THE INVENTION

Figure 1:
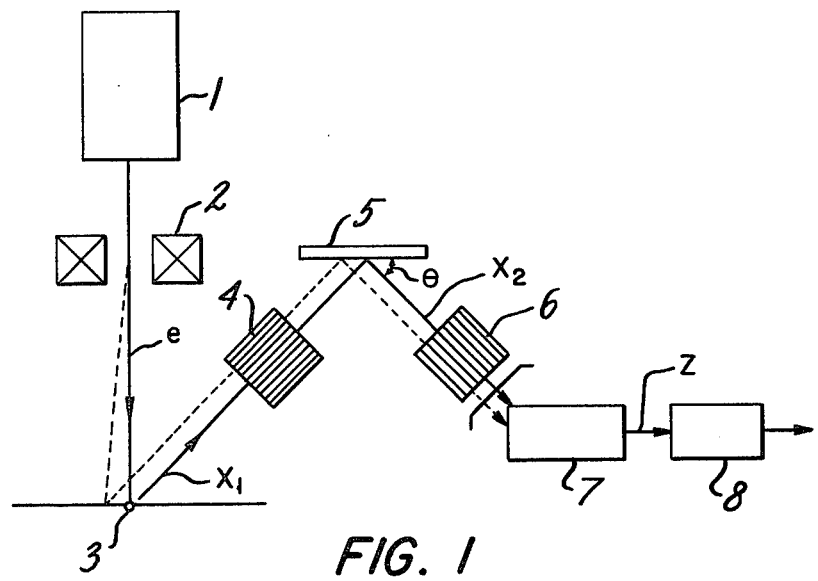
FIG. 1 shows the structure of the embodiment of the present invention.

FIG. 1 shows the entire structure of an analyzer according to the invention wherein numeral 1 is an electronic gun, 2 is an electronic lens, "e" is an electron beam, 3 is a sample or target object to be analyzed, X is an X-ray beam, 4 and 6 are solar slit members and 4 is output slit and 6 is input slit, 5 is a spectrocrystal for diffracting X-rays, 7 is an X-ray detector, and 8 is an operation circuit.

Figure 2A:
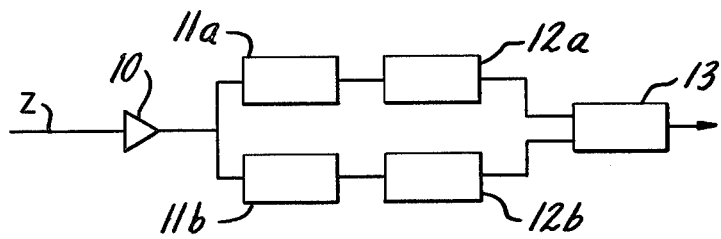
FIGS. 2a, b and c show block diagrams of the operation circuit of FIG. 1.
Figure 2B:
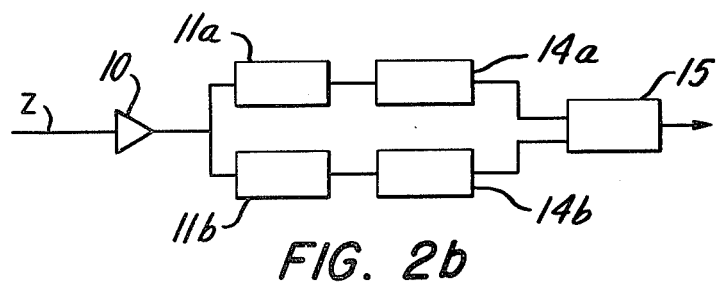
Figure 2C:
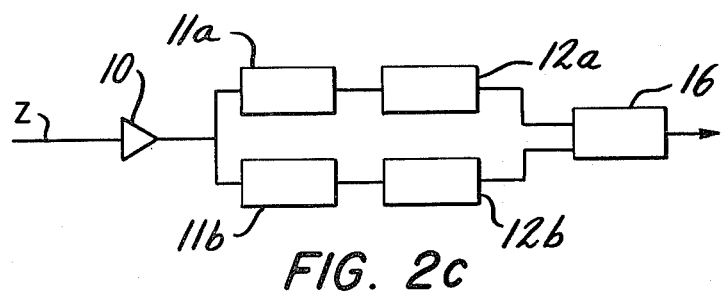

FIGS. 2a, 2b, 2c show detailed circuit block diagram of the operation circuit 8, and the different Figs. show different embodiments respectively.

The operation circuit 8 is composed of an amplifier 10, wave height discriminators 11a and 11b, counters 12a and 12b and a divider 13. However it is possible to replace the divider 13 by an analogue divider 15 by using rate meters 14a and 14b instead of the counter 12 such as shown in FIG. 2b. Furthermore it is possible to use a CPU 16 instead of the divider 12 as shown in FIG. 2c whereby it operates the same as FIG. 2a.

Figure 3:
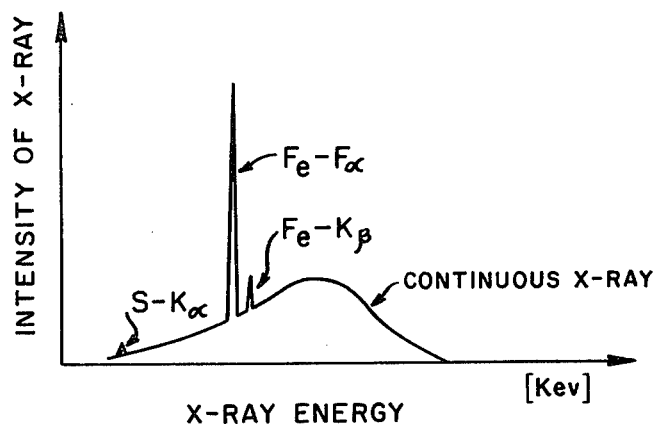
FIG. 3 shows a distribution characteristic of X-ray emitted from a sample.

In the case of using a macroanalyzer for analysis of a slab member such as a steel material, X-ray $X_1$ has an intensity distribution as shown in FIG. 3. In FIG. 3, characteristic X-rays Fe-K$\alpha$ and Fe-K$\beta$ from main components of the slab material are generated on a continuous X-ray spectrum, however, a characteristic X-ray of sulfur as shown by S-K$\beta$ is generated when impurities for example, sulfur in said slab member, are detected. The X-ray $X_1$ is incident on the spectrocrystal 5 through the output slit 4 whereby only X-rays of a particular wave length and an integer wave length thereof are picked up according to a reflection angle $\theta$ of X-ray $X_2$ by the spectrocrystal 5.

The angle $\theta$ is obtained by the Bragg expression as follows:

$$2d \sin \theta = n\lambda \text{ (n is the second degree)}$$

Figure 4:
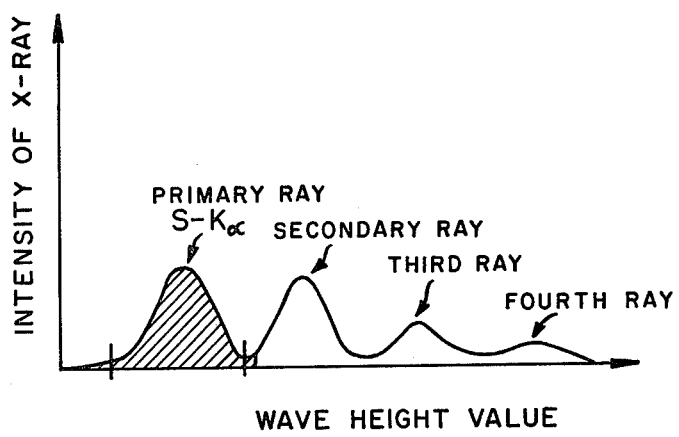
FIG. 4 shows a distribution characteristic of X-ray separated by a spectrocrystal.

Therefore, if we select the angle $\theta$ according to the wave length "$\lambda$" of the characteristic X-ray of sulfur, the characteristic X-rays of sulfur S-K$\alpha$ and high order X-ray are detected by X-ray detector 7 whereby an electric pulse signal as shown in FIG. 4 is generated. In this occasion, the charaoteristic X-ray signal S-K$\alpha$ is only involved as a primary-ray, the secondary-ray values are only continuous X-ray signals.

X-ray $X_1$ from the sample 3 is different according to an irradiation position of the electron beam "e" whereby the passing position of the X-ray relative to the solar slits 4 and 6 is moved everytime. An irregularity in spacing between the plates of the solar slit members 4 and 6 is very difficult to eliminate since the space between plates for the solar slits 4 and 6 is about 50-100 micron. Consequently an intensity of the X-ray output is irregular as shown in FIG. 5a resulting from a difference of the passing position of the X-rays.

Figure 5A:
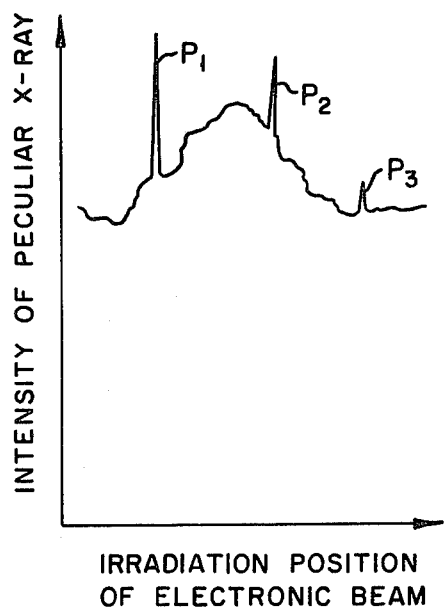
FIG. 5a shows a correlation between irradiation position of an electronic beam and intensity of X-ray detection signal.
Figure 5B:
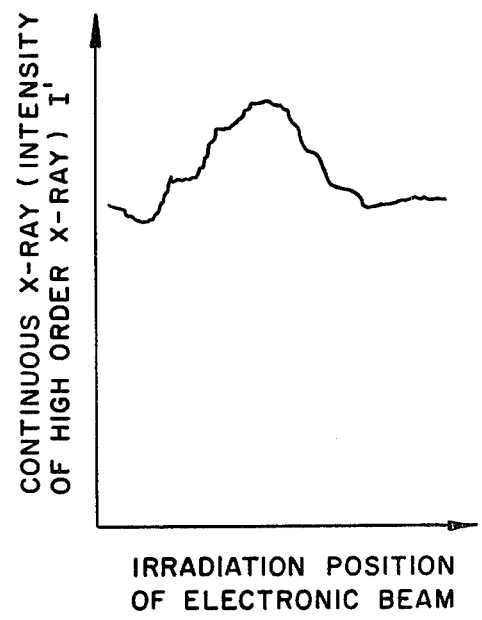
FIG. 5b shows an intensity characteristic of the high order X-ray in FIG. 4.
Figure 6:
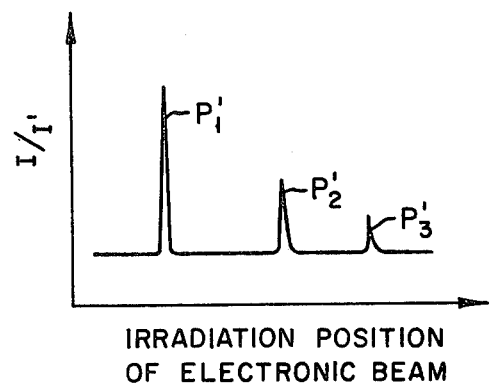
FIG. 6 shows intensity against irradiation position of an electronic beam derived from an output of the operation circuit in FIG. 1.

In case of analysis of a slab in which the size of the sample 3 is more than 10 cm×30 cm, it is necessary to scan an irradiation position of the electron beam "e" for a surface analysis in a high speed condition, therefore, it is very difficult to analyze the values of signals $P_1$, $P_2$ $P_3$ when the X-ray is detected as shown in FIG. 5a. However, it is possible to eliminate the effect of position irregularity of the slit as shown in FIG. 5a. Namely only a primary ray which includes S-K$\alpha$ of FIG. 4 is discriminated from an output of the X-ray detector 7 by a wave height discriminator 11a in the operation circuit 8 of FIG. 1. Additionally a signal of a high order ray is discriminated by a wave height discriminator whereby an output of counter 12b shows an intensity of the continuous X-ray spectrum as shown in FIG. 5b. Therefore, an output of divider 13 in which an output of counter 12a is divided by an output of counter 12b is shown in FIG. 6, and the signals $P_1'$, $P_2'$ and $P_3'$ are exactly measured. An absolute intensity of the continuous X-ray spectrum is almost unchanged in spite of a change of the irradiation position of the electron beam "e" (since the amount of iron in a slab member compared to the impurities is more than 99%), therefore a change of FIG. 5b definitely depends on a difference of the passing position of the slit member.

Said slab material as a sample includes sulfur, carbon, phosphor, aluminum, silicon and manganese. There are a plurality of solar slits 4 and 6 which are positioned at different values of angle $\theta$ around the sample 3 against different wave length values of the characteristic X-ray for many elements, the spectrocrystal 5 and X-ray detector 7.

According to the present invention, the irregularity of the slit member is canceled by the characteristic X-ray signal and the continuous spectrum X-ray signal from the solar slit and spectrocrystal being respectively divided whereby it is possible to provide a macroanalyzer which be able to effectively detect any impurities and extraction.

Furthermore, it is possible to obtain an intensity of X-ray at measuring points by obtaining an average value OVS/I/ ' of value I' at said measuring points as a new correct value, said average value OVS/I/ ' is obtained by the formula as follows:

$$\bar{I} = \frac{1}{n} \sum_{n=1}^{n} I'n$$

where

I'n is Intensity of the X-ray at measuring points be obtained by a beam scan which is parallel to the slit plate.

n is Number of measuring points by a beam scan which is parallel to the slit plate.

Furthermore, it is possible to obtain the same improvement by correcting a position irregularity in a slit of I according to said OVS/I/ ' by obtaining said OVS/I/ ' in every scan line according to a standard sample such as malleable iron.

I claim:

1. A macroanalyzer comprising: an electron gun for emitting an electron beam; an electron lens positionsed for collimating the electron beam to a very small diameter which is small relative to the size of a target object to be analyzed and for scanning the collimated electron beam across a target object while maintaining the very small diameter of the beam; a flat diffraction crystal for diffracting secondary X-rays emitted from the target object as the electron beam is scanned thereacross; a first solar slit member positioned to collimate the secondary X-rays emitted from the target object before the secondary X-rays reach said diffraction crystal; a second solar slit member positioned to collimate X-rays diffracted from the diffraction crystal; the first and second solar slit members each comprising a plurality of stacked parallel plates with a slit formed between each two adjoining plates; an X-ray detector positioned to detect X-rays passed through said second solar slit member and to generate an output signal representative of the detected X-rays; and circuit means receptive of the X-ray detector output signal for discriminating between detected characteristic X-rays and a detected continuous X-ray spectrum and for dividing the respective discrimination X-ray values to eliminate X-ray intensity irregularities in the detected values of the characteristic X-rays caused by the X-rays passing through said solar slit members.

2. A macroanalyzer according to claim 1, wherein said circuit means is comprised of:
   a pair of wave height discriminators each receptive of the X-ray detector output signal, and each set to discriminate a different wave height;
   a pair of counters each connected for counting the output of a respective one of said wave height discriminators; and
   dividing means for dividing the respective counts developed by said pair of counters.

3. A macroanalyzer according to claim 1, wherein said circuit means is comprised of:
   a pair of wave height discriminators each receptive of the X-ray detector output signal, and each set to discriminate a different wave height;
   a pair of rate meters each connected for counting the output of a respective one of said wave height discriminators; and
   an analog divider circuit for dividing the respective outputs developed by said pair of rate meters.

* * * * *